(12) United States Patent
Eurlings et al.

(10) Patent No.: US 10,495,889 B2
(45) Date of Patent: Dec. 3, 2019

(54) BEAM HOMOGENIZER, ILLUMINATION SYSTEM AND METROLOGY SYSTEM

(71) Applicants: ASML Netherlands B.V., Veldhoven (NL); ASML Holding N.V., Veldhoven (NL)

(72) Inventors: Markus Franciscus Antonius Eurlings, Tilburg (NL); Armand Eugene Albert Koolen, Nuth (NL); Teunis Willem Tukker, Eindhoven (NL); Johannes Matheus Marie De Wit, Helmond (NL); Stanislav Smirnov, Danbury, CT (US)

(73) Assignees: ASML Netherlands B.V., Veldhoven (NL); ASML Holding N.V., Veldhoven (NL)

( * ) Notice: Subject to any disclaimer, the term of this patent is extended or adjusted under 35 U.S.C. 154(b) by 0 days.

(21) Appl. No.: 15/439,856

(22) Filed: Feb. 22, 2017

(65) Prior Publication Data
US 2017/0248794 A1  Aug. 31, 2017

Related U.S. Application Data

(60) Provisional application No. 62/299,723, filed on Feb. 25, 2016.

(51) Int. Cl.
*G02B 27/09* (2006.01)
*G01B 11/27* (2006.01)
*G01N 21/49* (2006.01)
(Continued)

(52) U.S. Cl.
CPC ........ *G02B 27/0988* (2013.01); *G01B 11/272* (2013.01); *G01N 21/49* (2013.01);
(Continued)

(58) Field of Classification Search
CPC ............ G02B 27/0988; G02B 27/0927; G02B 26/008; G02B 27/0994; G02B 6/0008;
(Continued)

(56) References Cited

U.S. PATENT DOCUMENTS

| 5,673,102 A | 9/1997 | Suzuki et al. |
| 6,285,443 B1 | 9/2001 | Wangler et al. |

(Continued)

FOREIGN PATENT DOCUMENTS

| CN | 102331688 A | 1/2012 |
| DE | 10 2008 041288 A1 | 4/2009 |

OTHER PUBLICATIONS

International Search Report and Written Opinion of the International Searching Authority directed to related International Patent Application No. PCT/EP2017/052627, dated May 18, 2017; 13 pages.

*Primary Examiner* — Jade R Chwasz
(74) *Attorney, Agent, or Firm* — Sterne, Kessler, Goldstein & Fox P.L.L.C.

(57) ABSTRACT

A beam homogenizer for homogenizing a beam of radiation and an illumination system and metrology apparatus comprising such a beam homogenizer as provided. The beam homogenizer comprises a filter system having a controllable radial absorption profile and configured to output a filtered beam and an optical mixing element configured to homogenize the filtered beam. The filter system may be configured to homogenize the angular beam profile radially and said optical mixing element may be configured to homogenize the angular beam profile azimuthally.

21 Claims, 6 Drawing Sheets

(51) Int. Cl.
*G01N 21/88* (2006.01)
*G03F 7/20* (2006.01)
*F21V 8/00* (2006.01)
*G02B 26/00* (2006.01)

(52) U.S. Cl.
CPC ..... *G01N 21/8806* (2013.01); *G02B 27/0927* (2013.01); *G03F 7/70075* (2013.01); *G03F 7/70191* (2013.01); *G03F 7/70616* (2013.01); *G03F 7/70633* (2013.01); *G01N 2201/0631* (2013.01); *G02B 6/0008* (2013.01); *G02B 26/008* (2013.01); *G02B 27/0994* (2013.01)

(58) Field of Classification Search
CPC .. G01B 11/272; G01N 21/49; G01N 21/8806; G01N 2201/0631; G03F 7/70075; G03F 7/70633; G03F 7/70191; G03F 7/70616
USPC .................. 359/885, 889, 891, 892
See application file for complete search history.

(56) References Cited

U.S. PATENT DOCUMENTS

| | | | |
|---|---|---|---|
| 7,705,331 B1* | 4/2010 | Kirk | G01N 21/956 250/306 |
| 9,063,006 B2* | 6/2015 | Jungwirth | F21S 8/006 |
| 2002/0075468 A1* | 6/2002 | Antoni | G03F 7/70075 355/67 |
| 2004/0257559 A1 | 12/2004 | Dieckmann | |
| 2005/0140957 A1 | 6/2005 | Luijkx et al. | |
| 2006/0050261 A1 | 3/2006 | Brotsack | |
| 2008/0113281 A1 | 5/2008 | Maul et al. | |
| 2010/0245792 A1* | 9/2010 | Bijnen | G03B 27/42 355/53 |
| 2011/0096316 A1 | 4/2011 | Brotsack | |
| 2015/0003103 A1* | 1/2015 | Tukker | G02B 27/0927 362/551 |

* cited by examiner

BEAM HOMOGENIZER, ILLUMINATION SYSTEM AND METROLOGY SYSTEM

This application incorporates by reference in its entirety U.S. Provisional Application No. 62/299,723, filed Feb. 25, 2016.

BACKGROUND

Field of the Invention

The present invention relates to methods and apparatus of lithography usable, for example, in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

In metrology, and particularly metrology using scatterometers, the homogeneity of the beam of radiation used for the measurement is important. Therefore it is desirable to improve homogeneity of such a beam and/or control thereof.

SUMMARY

An embodiment of the present invention in a first aspect provides beam homogenizer for homogenizing a beam of radiation comprising: a filter system comprising a controllable radial absorption profile and configured to output a filtered beam; and an optical mixing element configured to homogenize the filtered beam.

Another embodiment of the present invention also comprises an illumination system comprising the beam homogenizer of the first aspect and a metrology apparatus comprising such an illumination system.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals, and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing embodiments of the invention in detail, it is instructive to present an example environment in which embodiments of the present invention may be implemented.

Figure 1:
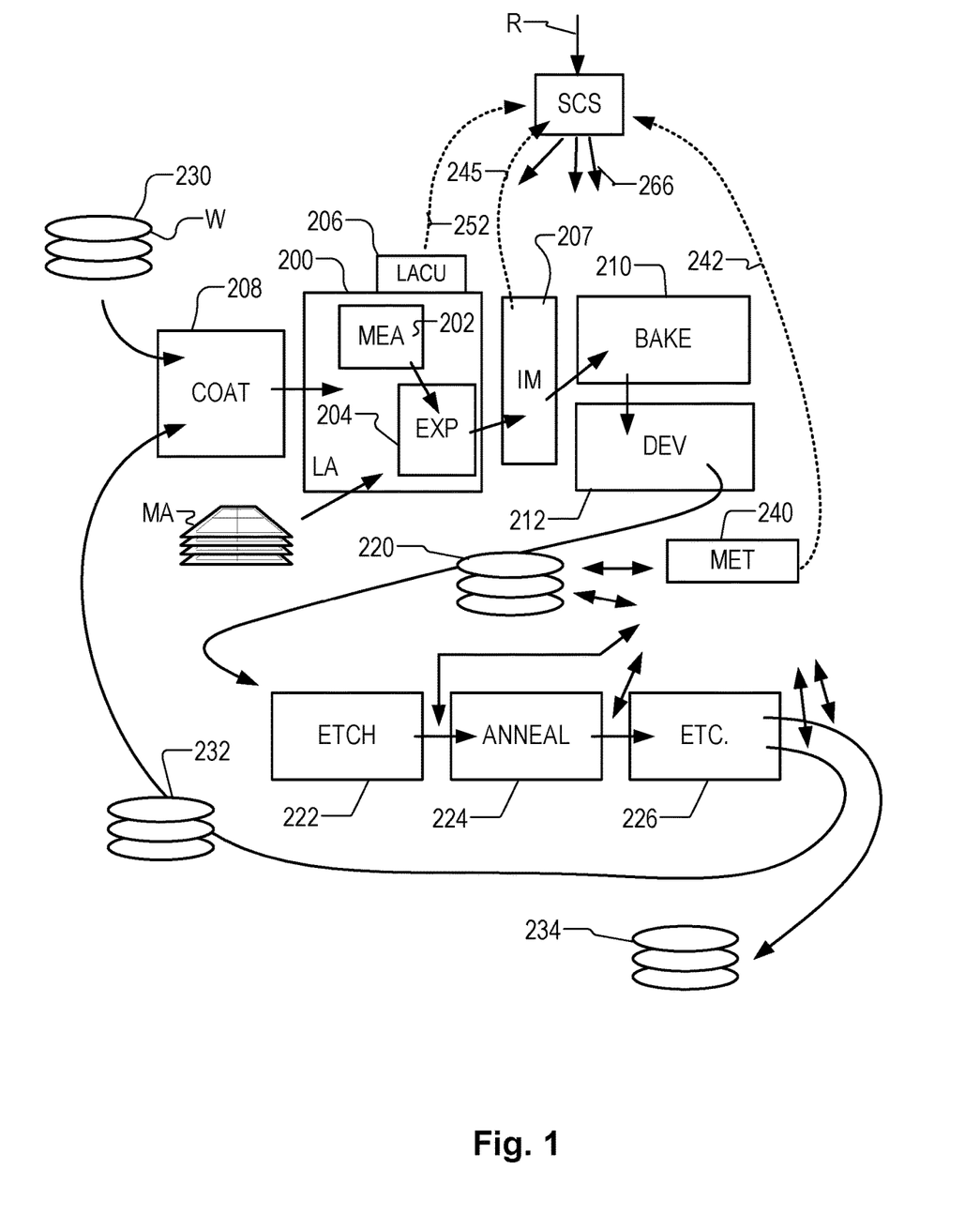
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc.

Accordingly a manufacturing facility in which litho cell LC is located may also include one or more metrology systems. The metrology systems may include a stand-alone metrology apparatus MET 240 and/or an integrated metrology apparatus IM 207. The stand-alone metrology apparatus MET 240 receives some or all of the substrates W that have been processed in the litho cell for performing measurements offline. The integrated metrology apparatus IM 207 performs inline measurements and is integrated into the track to receive and measure some or all of the substrates W immediately after exposure. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed.

A common example of a metrology apparatus in a modern lithographic production facility is a scatterometer, for example an angle-resolved scatterometer or a spectroscopic scatterometer, and it may normally be applied to measure properties of the developed substrates at 220 prior to etching in the apparatus 222. Using stand-alone metrology apparatus 240 and/or integrated metrology apparatus 207, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Figure 2A:
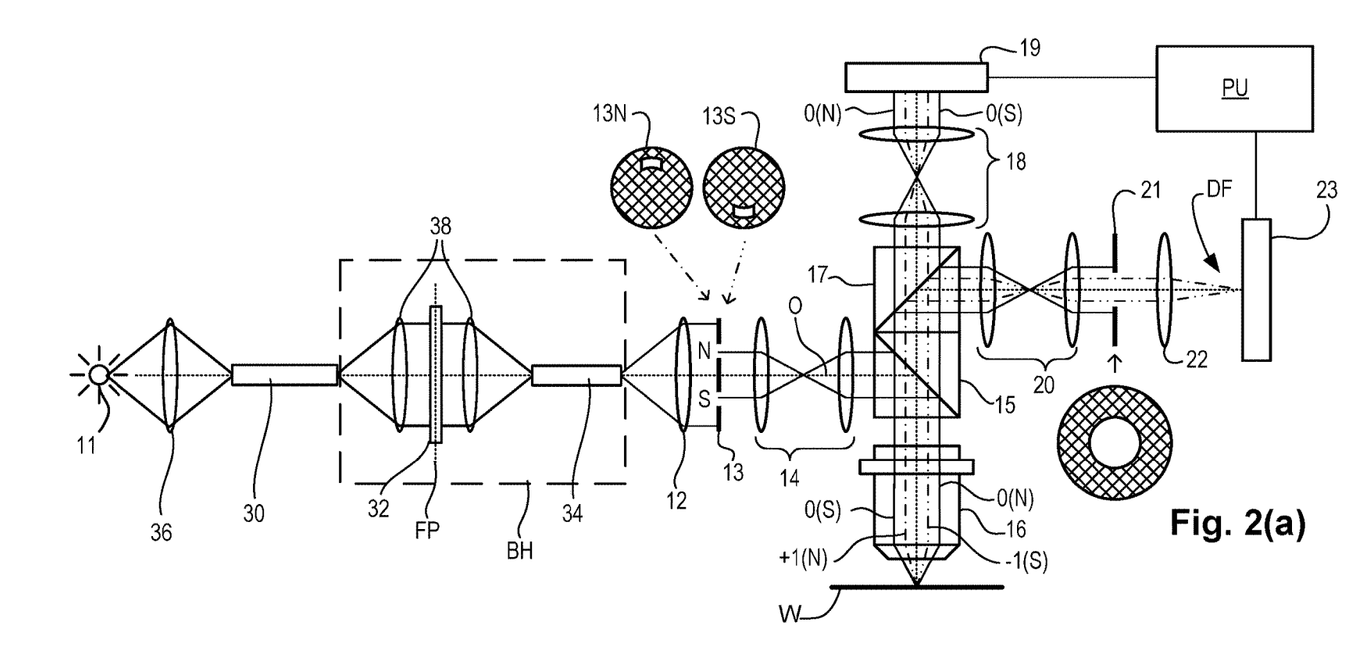
FIGS. 2(a)-2(b) comprise (a) a schematic diagram of a dark field scatterometer according to an embodiment of the invention for use in measuring targets using a first pair of illumination apertures, (b) a detail of diffraction spectrum of a target grating for a given direction of illumination.

A metrology apparatus is shown in FIG. 2(a). The stand-alone metrology apparatus 240 and/or the integrated metrology apparatus 207 may comprise such a metrology apparatus, for example, or any other suitable metrology apparatus. A target T and diffracted rays of measurement radiation used to illuminate the target are illustrated in more detail in FIG. 2(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via beam homogenizer BH (which will be described in detail below) and beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

Figure 2B:
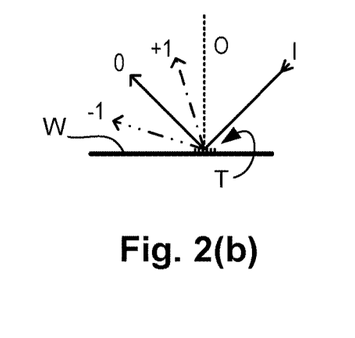
Figure 3A:
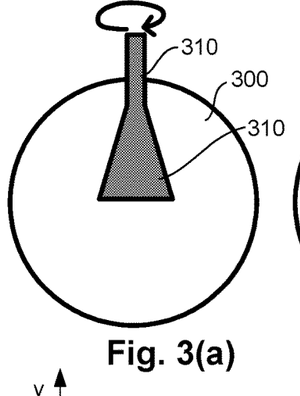
FIGS. 3(a)-3(c) illustrate a first arrangement for a filter system comprised within a beam homogenizer according to an embodiment of the invention, in (a) a first configuration, (b) a second configuration and (c) a third configuration.
Figure 3B:
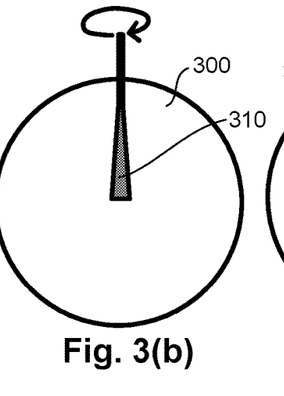
Figure 3C:
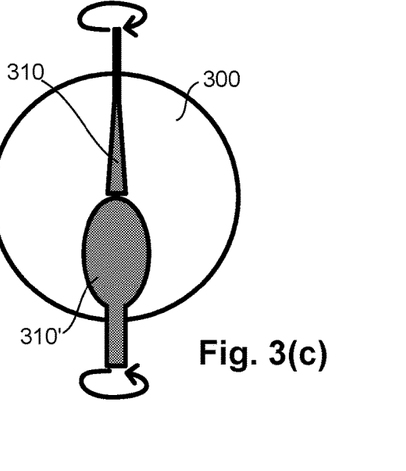

As shown in FIG. 2(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 2(a) and 2(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 2(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 2 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 2) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

For metrology, an important criterion is beam homogeneity, that is the (intensity) homogeneity of the beam of measurement radiation. The beam of measurement radiation should be as homogenous as possible. This is true for both field planes and pupil planes. Presently, there is no means for adjusting beam homogeneity in a metrology apparatus, other than changing parts or modules.

It is therefore proposed to provide a beam homogenizer, and in particular an adjustable beam homogenizer, suitable for a metrology apparatus, and for a metrology apparatus having such a beam homogenizer. FIG. 2(a) shows such a beam homogenizer BH forming part of a metrology apparatus. The beam homogenizer BH comprises a filter system 32 and an optical mixing element 34 in series. Radiation from the illumination source 11 is shown (optionally) focused by a lens element 36 into an illumination fiber 30 which transports the radiation to the beam homogenizer BH. In other embodiments, the lens element 36 and illumination fiber 30 may be comprised with the beam homogenizer BH.

The input of the beam homogenizer BH comprises optics 38 which define a filter plane FP. The filter system 32 is located on or near to the filter plane FP, and the filtered radiation mixed by optical mixing element 34. The filter plane FP may be at a pupil plane (or pupil-like plane, e.g., a conjugate pupil plane) of the system, or at a point not exactly at the conjugate pupil plane. The latter example allows blurring in the actual pupil plane downstream, which may help when using pixelated filter elements in the filter system 32 (such as in the example illustrated in FIG. 7 and described below). It may be advantageous to blur such pixelated filter elements into a smooth pattern.

In an embodiment, the optical mixing element 34 is an optical mixing element which uses chaotic billiard theory. Such an optical mixing element may be an elongate element comprising a cross-sectional shape (transverse to its length) which is neither a circle nor regular polygon. The optical mixing element may, for example, take any of the forms described and/or illustrated in US2015/0003103, which is herein incorporated by reference in its entirety. However, the concepts described herein are not limited to these forms, and other forms could be used in their place. The optical mixing element will be described in greater detail below.

Of most relevance is that such an optical mixing element 34 homogenizes a radiation beam very well spatially, but only homogenizes the angular beam profile in part. This angular part-homogenization breaks down into very good azimuthal homogenization, but poor or no radial homogenization.

It is therefore proposed to use the filter system 32 to control the radial (e.g., intensity) profile of the radiation entering the optical mixing element. The control of the angular radial profile may be such that the radiation is radially homogenized. Radially homogenized radiation entering a chaotic billiard optical mixing element 34 as described herein, will be further homogenized spatially and azimuthally, and therefore will be homogenized fully.

In an embodiment, the filter system 32 may comprise a controllable absorption profile to control the radial profile of the radiation exiting the filter system. This can be done by providing one or more filter elements with a variable profile. The profile may be made varied, for example, by providing one or more filter elements having a configurable absorption profile. The configurable absorption profile may be achieved by, for example, changing a filter element's rotational position and/or orientation, providing multiple interchangeable filter elements with different profiles, providing one or more patterned filter elements with configurable pattern and/or providing two or more filter elements which act together to provide a configurable (neutral density) absorption profile. This is a non-exhaustive list of examples, and it should be understood that combinations of any of the above are possible.

In an embodiment, the filter system 32 may only filter a radial portion of the beam (illumination field). As such, in an embodiment, the filter system may be configured to only filter a portion of the beam cross section between a center region and an edge region. This radial filtering may be controlled to provide an absorption profile which results in a homogenous radial intensity profile of the beam between these points. Subsequent homogenization by the optical mixing element, spatially and over 360 degrees azimuthally, will then fully homogenize the beam.

FIGS. 3 to 7 illustrate a number of these possible arrangements for the filter system 32. FIGS. 3(a) and (b) shows an illumination field (e.g., pupil) 300 with a filter element 310 having a profile which varies with its orientation. FIG. 3(a) shows the filter element 310 in a first orientation and FIG. 3(b) shows the same filter element 310 having been rotated around its longitudinal axis such that it is in a second orientation. In this second orientation, the profile of the filter element 310 is different than in the first orientation. It may be that the profile varies continuously or stepwise as it is rotated, providing a continuously variable profile or number of different profiles. It is further possible that the filter element 310 be movable within the field, either horizontally (x-direction), vertically (y-direction) or both to provide a further control of the radial illumination profile. FIG. 3(c) shows an embodiment with two filter elements 310, 310'. One or both filter elements may have a profile dependent on orientation as described, and each may have different or similar configurations. The filter element(s) may have any shape or size and may extend further, or not extend as far, in either x or y direction compared to the examples shown.

Figure 4:
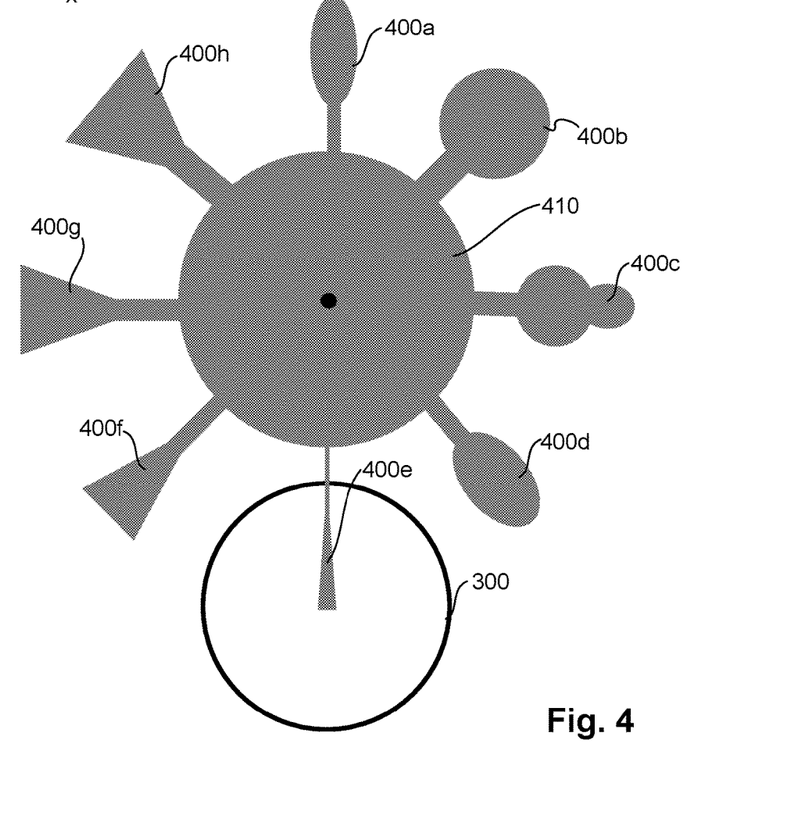
FIG. 4 illustrates a second arrangement for a filter system comprised within a beam homogenizer according to an embodiment of the invention.
Figure 5A:
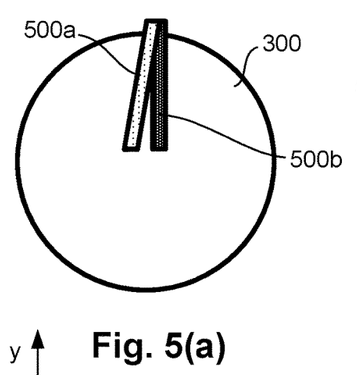
FIGS. 5(a)-5(m) illustrate a third arrangement for a filter system comprised within a beam homogenizer according to an embodiment of the invention in (a)-(g) a number of different configurations and (h)-(m) corresponding absorption profiles for the different configurations.
Figure 5B:
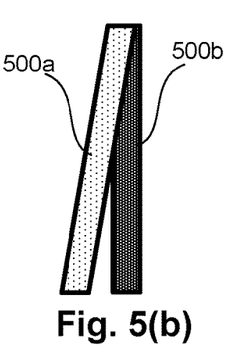
Figure 5C:
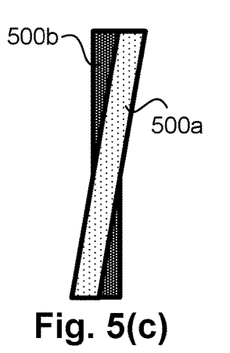
Figure 5D:
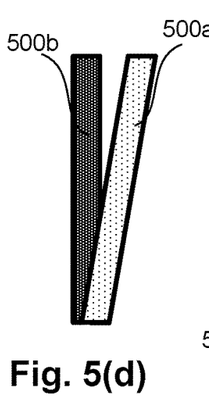
Figure 5E:
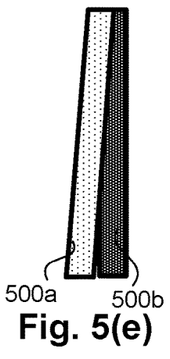
Figure 5F:
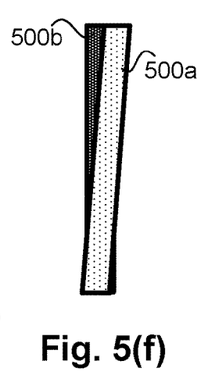
Figure 5G:
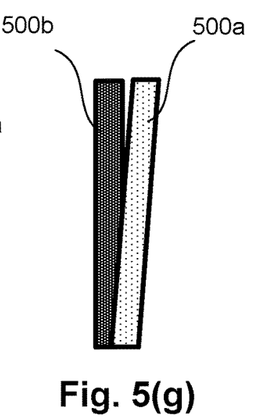
Figure 5H:
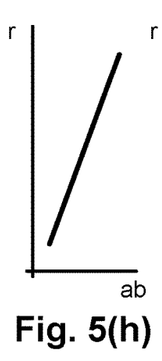
Figure 5I:
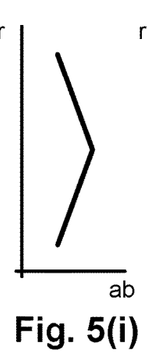
Figure 5J:
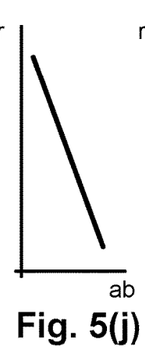
Figure 5K:
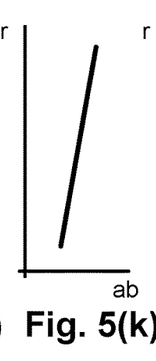
Figure 5L:
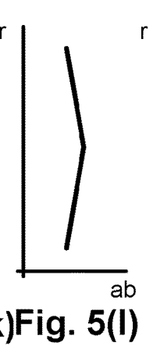
Figure 5M:
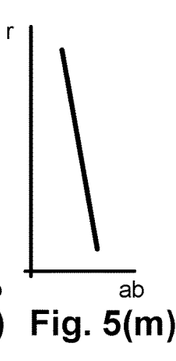
Figure 6A:
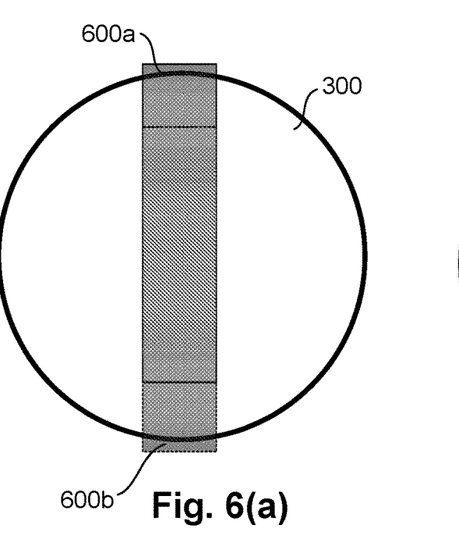
FIGS. 6(a)-6(d) illustrate a fourth arrangement for a filter system comprised within a beam homogenizer according to an embodiment of the invention in (a)-(d) a number of different configurations.
Figure 6B:
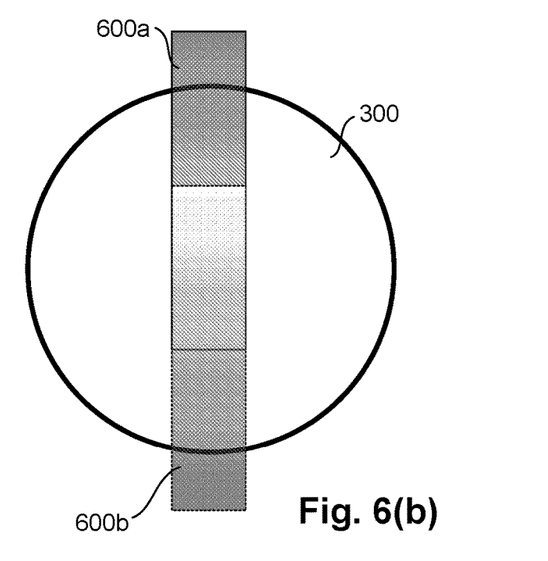
Figure 6C:
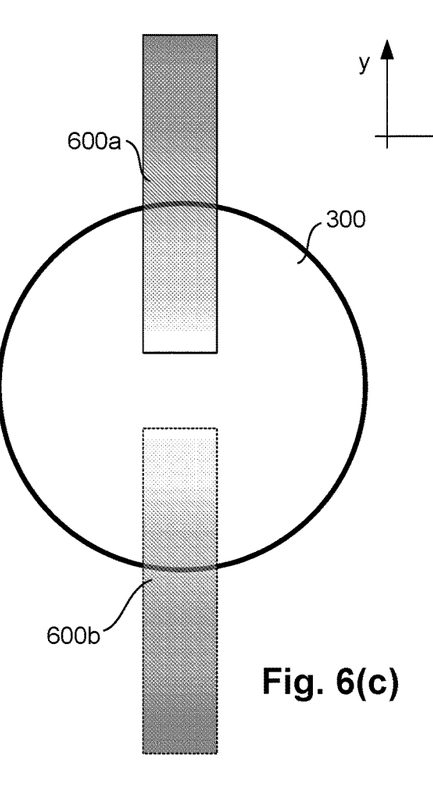
Figure 6D:
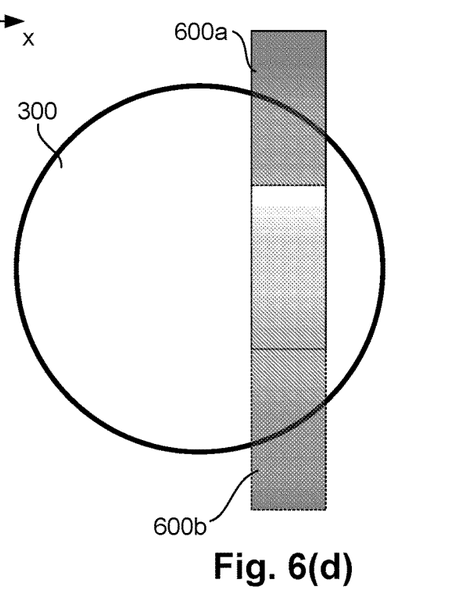

FIG. 4 shows an arrangement having a plurality of filter elements 400a-400h, one (or more) of which can be moved into the illumination field 300 as appropriate. In the embodiment shown, the filter elements are mounted to a wheel 410, such that rotation of the wheel 410 around its center moves different ones of said plurality of filter elements 400a-400h into the illumination field 300. Of course, different arrangements for swapping different filter elements are possible. Also possible are arrangements which swap two filter elements 400a-400h into the illumination field 300 at one time (in a manner similar to that illustrated in FIG. 3(c)); for example by having two wheels, i.e., an additional second wheel below the illumination field 300, which also comprises a plurality of filter elements. Such an arrangement can also be combined with the arrangement of FIG. 3, such that one or more of the filter elements 400a-400h may be rotatable relative to the wheel around its axis, to provide a variable profile.

FIG. 5 shows an arrangement comprising two or more filter elements 500a, 500b which are arranged to partially overlap, with at least one of them moveable such that they can be moved relative to each other (e.g. in the x-direction). In an embodiment, the filter elements 500a, 500b may be two (e.g., similar) elongate elements at different orientations, and/or arranged such that one or both may have variable orientation. FIG. 5(a) shows the filter elements 500a, 500b in a first configuration within the illumination field 300. FIGS. 5(b) to 5(d) show the filter elements 500a, 500b in the same orientation, but different configurations, being in different relative positions in each diagram. FIGS. 5(e) to 5(g) show the filter elements 500a, 500b in the same relative positions as illustrated in FIGS. 5(b) to 5(d) but with filter element 500a at a different orientation than that illustrated in FIGS. 5(b) to 5(d). FIGS. 5(h) to 5(m) each show an absorption profile of the absorption ab against radius r (from center) for the configurations depicted in FIGS. 5(b) to 5(g) respectively. Each of the filter elements 500a, 500b may comprise opaque structures or patterns on a transparent element (e.g., glass plate), for example.

FIG. 6 shows an arrangement having two or more filter elements, each comprising a neutral density transmissive filter plate 600a, 600b, each with an absorption profile, f(r) and g(r) respectively (where r is radius). The two neutral density filter plates 600a, 600b are placed such that they overlap within the illumination field 300. By enabling relative movement of the neutral density filter plates 600a, 600b, thereby changing the relative distance Dr between them, a variable, controllable absorption profile h(r,Dr)=f(r)*g(r−Dr) is obtained. Further control may be obtained by changing the profiles of filter plates 600a, 600b (e.g., by swapping them with others). FIGS. 6(a) and 6(b) show the filter elements 600a, 600b in different configurations, being in different relative positions in each diagram. FIG. 6(c) shows a further configuration where the position of filter elements 600a, 600b is controllable in the x-direction, providing a further control possibility. This latter control in the x-direction can equally be applied to any of the other filter elements described above.

Figure 7A:
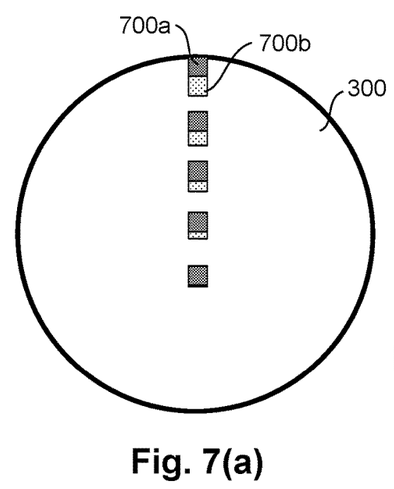
FIGS. 7(a)-7(d) illustrate a fifth arrangement for a filter system comprised within a beam homogenizer according to an embodiment of the invention in (a)-(d) a number of different configurations.

FIG. 7 shows an arrangement in which the Moiré effect of two similar, but not identical, patterns is exploited. For example, as shown, there may be two filter elements 700a, 700b, each comprising a repeating pattern of sub-features, where the pitch of these sub-features is slightly different for the two filter elements 700a, 700b. The filter elements should overlap and be moveable relative to each other (i.e., one or both can move relative to the other) in the direction of the repeating pattern, for example in the y-direction (although an x-direction Moiré pattern is possible), thus altering the resultant Moiré pattern and therefore the absorption profile. FIG. 7(a) shows the filter elements 700a, 700b in a first configuration within the illumination field 300.

Figures 7B, 7C, 7D:
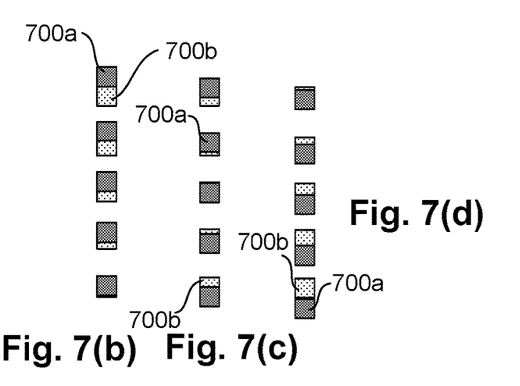

FIGS. 7(b) to 7(d) show the filter elements 700a, 700b in different configurations, being in different relative positions in each diagram.

A benefit of the concepts described herein is that the filter system implementation can be simplistic since the filter system itself does not have to take care of the homogeneity, other than providing a suitable average radial intensity profile. This makes many implementations possible, for example, using a simple 1 axis or 2 axis actuator for the filter elements.

In an embodiment, the metrology apparatus may comprise means for measuring the homogeneity of the beam. Such means already exist on some metrology apparatuses, and for example could include the camera 19 of FIG. 2, or any other such camera or sensor means. Any non-homogeneity detected can form the basis of calculated corrections for control of the filter system in a feedback loop. In this way, a suitable level of beam homogeneity can be maintained.

Turning again to the optical mixing element, this may comprise an elongated optical mixing element. The optical mixing element may be made of a transparent material like glass or plastic and may comprise an entry face and an exit face. At operation, a bundle of light rays is directed towards the entry face, wherein the bundle of light rays undergoes total internal reflection (TIR) at the interfaces towards the surrounding medium. After being reflected within the optical mixing element, the bundle of light rays exits the optical mixing element through the exit face.

Any configuration and cross-sectional profile is possible which achieves chaotic mixing of the radiation as it internally reflects multiple times within the optical mixing element 34. The number of possible designs are too numerous to list. The optical mixing element may comprise an elongated optical element arranged for homogenizing light, said optical mixing element comprising a transversal entry face and a transversal exit face, and having a cross section which has no stable paths i.e., paths for which a ray returns to the same x,y coordinate with the same direction (z is along the length of the optical mixing element). Of course, there may be differences in the degree of mixing between different cross section designs, with some cross sections mixing better than others (higher Lyaponov coefficients). For these, the optical mixing element can be shorter. For a fiber having a length of 3 meters any differences will become small. As such, the cross section of the optical mixing element may have:

1) A periphery comprising at least one curved section; and
2) An absence of opposing edges which are parallel (a stable path would occur between such parallel edges, i.e., no mixing would happen).

In an embodiment, the total length of the curved section(s) constitutes at least 1% of the length of said perimeter.

Figure 8:
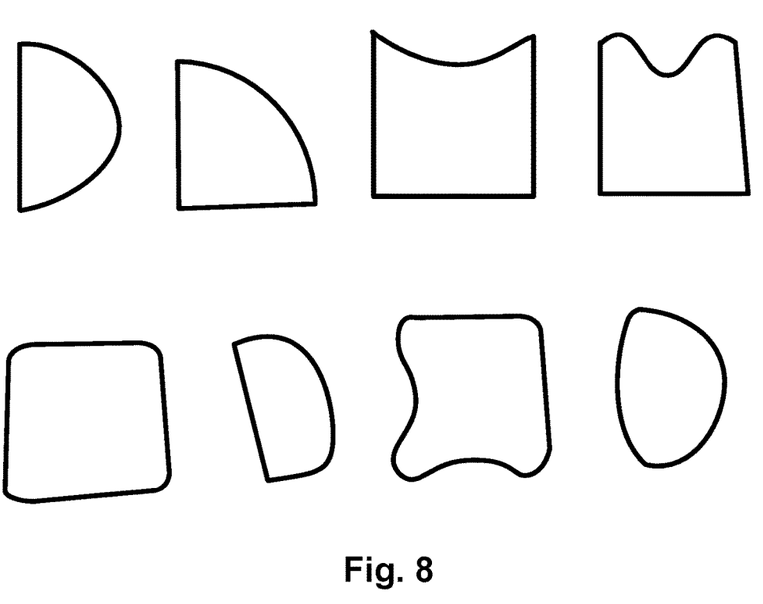
FIG. 8 illustrates a number of alternative cross-section shapes for an optical mixing element used in embodiments of the invention.

In embodiments, the cross section of the optical mixing element may have a perimeter shaped as a convex or concave shape (or partially both) and may comprise any number (including zero) of edges zero curvature. The number of curved and non-curved perimeter elements does not have to be equal. Also sections of negative curvature (concave) are also possible. Cross section shapes can include, in addition to those described in US2015/0003103, shapes formed of inter alia two joined arcs (of the same or different curvature), an arc and straight line forming a "D" shape or similar, an arc and two straight lines in the form of a circle segment or similar, shapes based on polygons, but having curved vertices and/or one or more sides with negative curvature, or sections of both positive and negative curvature (e.g., "wavy"). FIG. 8 shows a variety of different alternative cross section shapes, provided purely by way of example. As already mentioned, the actual shape could be one of a number of alternatives too numerous to describe each one here. It is to be understood that any shape which promotes chaotic mixing can be used.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A beam homogenizer for homogenizing a beam of radiation comprising:
    a filter system configured to receive and filter the beam, the filter system comprising:
        a controllable radial absorption profile; and
        a filter element configured to:
            adjust the controllable radial absorption profile to adjust a radial intensity distribution of the beam; and
            homogenize the beam radially based on the adjusted radial intensity distribution; and
    an optical mixing element configured to receive and further homogenize the filtered beam from the filter system and output a homogenized beam.

2. The beam homogenizer of claim 1, wherein the optical mixing element is further configured to homogenize the filtered beam azimuthally.

3. The beam homogenizer of claim 2, wherein the optical mixing element is further configured to homogenize the filtered beam spatially.

4. The beam homogenizer of claim 1, wherein the filter system is configured to filter only a radial portion of the beam.

5. The beam homogenizer of claim 1, wherein the filter system further comprises a plurality of interchangeable filter elements configured to adjust the controllable radial absorption profile.

6. The beam homogenizer of claim 5, wherein the plurality of interchangeable filter elements are mounted on a wheel such that selective rotation of the wheel allows one or more of the plurality of interchangeable filter elements to be moved into an illumination field of the beam.

7. The beam homogenizer of claim 5, wherein one or more of the plurality of interchangeable filter elements is configured to move from a radial portion of the beam.

8. The beam homogenizer of claim 1, wherein:
    the filter element comprises a longitudinal axis that is perpendicular to an optical axis of the beam; and
    the filter element is rotatable around the longitudinal axis so as to adjust an area of influence of the filter element in an illumination field of the beam and thereby adjust the controllable radial absorption profile.

9. The beam homogenizer of claim 1, wherein:
    the filter system further comprises a second filter element;
    the filter element is configured to partially overlap the second filter element,
    the filter element is configured to move relative to the second filter element and/or the second filter element is configured to move relative to the filter element, and the controllable radial absorption profile depends on a position of the filter element relative to a position of the second filter element.

10. The beam homogenizer of claim 9, wherein the filter element and the second filter element are elongated elements and relative movement between the filter element and the second filter element comprises rotational movement.

11. The beam homogenizer of claim 9, wherein the filter element comprises a first repeating pattern of sub-features and the second filter element comprises a second repeating pattern of sub-features such that the overlapping of the filter element and the second filter element results in a Moiré pattern that depends on the position of the filter element relative to the position of the second filter element.

12. The beam homogenizer of claim 9, wherein each of the filter element and the second filter element comprises a neutral density transmissive filter having an absorption profile.

13. The beam homogenizer of claim 1, wherein the optical mixing element comprises an optical chaotic mixing element comprising:
    a transversal entry face and a transversal exit face, the entry face configured to receive the filtered beam passed through the filter system; and
    a perimeter shaped such that radiation travelling between the transversal entry face and the transversal exit face is chaotically mixed.

14. The beam homogenizer of claim 13, wherein the perimeter comprises:
    one or more curved sections; and
    an absence of parallel opposing edges.

15. The beam homogenizer of claim 13, wherein a total length of the one or more curved sections constitutes at least 1% of a length of the perimeter.

16. The beam homogenizer of claim 1, further comprising:
    a homogenization detector configured to measure a homogenization of the homogenized beam; and
    a controller configured to control the filter system to correct for any measured beam non-homogenization.

17. The beam homogenizer of claim 1, wherein the controllable radial absorption profile adjusted by the filter element comprises an absorption that decreases with respect to an increasing distance from the center of an illumination field of the beam.

18. The beam homogenizer of claim 1, wherein the controllable radial absorption profile adjusted by the filter element comprises an absorption that initially increases with respect to an increasing distance from the center of an illumination field of the beam and then decreases with respect to the increasing distance from the center of the illumination field before reaching an edge of the illumination field.

19. An illumination system comprising:
    a beam homogenizer configured to homogenize a beam of radiation, the beam homogenizer comprising:
        a filter system configured to receive and filter the beam, the filter system comprising:
            a controllable radial absorption profile; and
            a filter element configured to:
                adjust the controllable radial absorption profile to adjust a radial intensity distribution of the beam; and
                homogenize the beam radially based on the adjusted radial intensity distribution; and an optical mixing element configured to receive and further homogenize the filtered beam from the filter system and output a homogenized beam.

20. The illumination system of claim 19, further comprising:
a homogenization detector configured to measure a homogenization of the homogenized beam; and
a controller configured to control the filter system to correct for any detected beam non-homogenization.

21. A metrology apparatus comprising:
an illumination system comprising:
a beam homogenizer configured to homogenize a beam of radiation, the beam homogenizer comprising:
a filter system configured to receive and filter the beam, the filter system comprising:
a controllable radial absorption profile; and
a filter element configured to:
adjust the controllable radial absorption profile to adjust a radial intensity of the beam; and
homogenize the beam radially based on the adjusted radial intensity distribution; and
an optical mixing element configured to receive and further homogenize the filtered beam from the filter system and output a homogenized beam; and
a detection system configured to detect scattered radiation arising from illumination of a structure on a substrate.

* * * * *